(12) United States Patent
Kim

(10) Patent No.: US 11,435,380 B2
(45) Date of Patent: Sep. 6, 2022

(54) SIGNAL MEASUREMENT APPARATUS AND SIGNAL MEASUREMENT METHOD

(71) Applicant: SAMSUNG ELECTRONICS CO., LTD., Suwon-si (KR)

(72) Inventor: Jongpal Kim, Seoul (KR)

(73) Assignee: Samsung Electronics Co., Ltd., Suwon-si (KR)

(*) Notice: Subject to any disclaimer, the term of this patent is extended or adjusted under 35 U.S.C. 154(b) by 138 days.

(21) Appl. No.: 16/778,156

(22) Filed: Jan. 31, 2020

(65) Prior Publication Data

US 2021/0088560 A1 Mar. 25, 2021

(30) Foreign Application Priority Data

Sep. 20, 2019 (KR) .................. 10-2019-0116252

(51) Int. Cl.
*G01R 19/00* (2006.01)
*H03K 5/24* (2006.01)
*H03F 3/45* (2006.01)
*G01N 27/22* (2006.01)
*A61B 5/053* (2021.01)

(52) U.S. Cl.
CPC ....... *G01R 19/0038* (2013.01); *G01N 27/228* (2013.01); *H03F 3/45475* (2013.01); *H03K 5/24* (2013.01); *A61B 5/053* (2013.01); *H03F 2200/129* (2013.01); *H03F 2203/45512* (2013.01); *H03F 2203/45526* (2013.01)

(58) Field of Classification Search
USPC .......................... 324/658, 679, 686
See application file for complete search history.

(56) References Cited

U.S. PATENT DOCUMENTS

| | | | |
|---|---|---|---|
| 7,385,443 B1 * | 6/2008 | Denison | A61B 5/7217 330/9 |
| 2012/0268145 A1 * | 10/2012 | Chandra | G06F 3/04166 324/686 |
| 2019/0183378 A1 * | 6/2019 | Mosesov | A61B 5/6869 |

FOREIGN PATENT DOCUMENTS

| | | |
|---|---|---|
| JP | 2012-157463 A | 8/2012 |
| KR | 10-0624446 B1 | 9/2006 |
| KR | 10-2016-0009982 A | 1/2016 |
| KR | 10-1674580 B1 | 11/2016 |
| KR | 10-2018-0033976 A | 4/2018 |

* cited by examiner

*Primary Examiner* — Vincent Q Nguyen
(74) *Attorney, Agent, or Firm* — NSIP Law

(57) ABSTRACT

A signal measurement apparatus and signal measurement method are provided. The measurement apparatus includes a compensation signal generating circuit configured to generate a target compensation signal that reduces a carrier frequency component in a voltage signal that is input into an amplifier based on an output signal of the amplifier, and the amplifier amplifies the voltage signal to which the target compensation signal is applied, wherein the compensation signal generating circuit is configured to determine a signal value of a subsequent compensation signal based on a signal value of the output signal of the amplifier amplified by applying a previous compensation signal, when determining the target compensation signal.

13 Claims, 8 Drawing Sheets

SIGNAL MEASUREMENT APPARATUS AND SIGNAL MEASUREMENT METHOD

CROSS-REFERENCE TO RELATED APPLICATIONS

This application claims the benefit under 35 USC § 119(a) of Korean Patent Application No. 10-2019-0116252 filed on Sep. 20, 2019 in the Korean Intellectual Property Office, the entire disclosure of which is incorporated herein by reference for all purposes.

BACKGROUND

1. Field

The following description relates to a signal measurement apparatus and a signal measurement method.

2. Description of Related Art

A body, for example, a human body, includes biological tissues having various electrical characteristics. The biological tissues have a conductivity through ions that may carry electric charges. Biological tissues of a different part of the body may have a different conductivity. Biological tissues of muscles may have a characteristic of a conductor that allows a flow of current, whereas biological tissues of bones may have a characteristic of a nonconductor that does not allow a flow of current. The biological tissues have electrical resistance characteristics or reactance characteristics. A portion of the biological tissues transmits a high-frequency input signal in an ohmic manner, and another portion of the biological tissues may transmit a low-frequency input signal in a capacitive manner. To measure the impedance of biological tissues, a small alternating current is applied to the biological tissues, and an alternating voltage induced by the corresponding alternating current is measured. The magnitude of the alternating current applied to the biological tissues is known information, and thus the bioimpedance may be estimated by analyzing the measured alternating voltage based on Ohm's law.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In a general aspect, a signal measurement apparatus includes a compensation signal generating circuit configured to generate, based on an output signal of an amplifier, a target compensation signal that reduces a carrier frequency component in a voltage signal that is input into the amplifier; wherein the target compensation signal is applied to the voltage signal; wherein the amplifier is configured to amplify the voltage signal to which the target compensation signal is applied, and wherein the compensation signal generating circuit is further configured to determine a signal value of a subsequent compensation signal based on a signal value of the output signal of the amplifier that is amplified by applying a previous compensation signal to the output signal of the amplifier, when determining the target compensation signal.

The compensation signal generating circuit may be further configured to search for the target compensation signal based on a change in the output signal of the amplifier resulting from a change in a signal magnitude of the previous compensation signal.

The compensation signal generating circuit may include a sample and hold circuit configured to sample the signal value of the output signal of the amplifier and hold the sampled signal value; a comparator configured to receive the signal value from the sample and hold circuit and output a comparison result; and a determiner configured to determine the signal value of the subsequent compensation signal based on the comparison result.

The comparator may be further configured to compare a first signal value of a first output signal of the amplifier and a second signal value of a second output signal of the amplifier, the first output signal and the second output signal included in a differential output signal of the amplifier, output a first comparison result value in response to the first signal value being greater than the second signal value, and output a second comparison result value different from the first comparison result value in response to the first signal value being less than or equal to the second signal value.

The comparator may be further configured to compare the signal value of the output signal of the amplifier to a reference signal value, output a first comparison result value in response to the signal value of the output signal of the amplifier being greater than the reference signal value, and output a second comparison result value different from the first comparison result value in response to the signal value of the output signal of the amplifier being less than or equal to the reference signal value.

The determiner may be further configured to determine the signal value of the subsequent compensation signal to be greater than a signal value of the previous compensation signal, in response to the first comparison result value being received from the comparator.

The determiner may be further configured to determine the signal value of the subsequent compensation signal to be less than a signal value of the previous compensation signal, in response to the second comparison result value being received from the comparator.

A variation of a signal value applied to determine the signal value of the subsequent compensation signal may be less than a variation of a signal value applied to determine the signal value of the previous compensation signal.

The subsequent compensation signal may be a digital signal, and wherein the compensation signal generating circuit may further include a converter configured to convert the determined signal value of the subsequent compensation signal into an analog voltage signal.

The converter may include a delayer configured to delay a phase of the subsequent compensation signal.

The signal measurement apparatus may include a first capacitor comprising a first end to which a voltage signal measured from a measurement object is transmitted, and a second end connected to an input terminal of the amplifier.

The target compensation signal and the voltage signal transmitted from the first capacitor may be in antiphase.

The signal measurement apparatus may include a second capacitor comprising a first end connected to the compensation signal generating circuit, and a second end connected to an input terminal of the amplifier.

In a general aspect, a signal measurement method performed by a signal measurement apparatus includes transmitting a current signal to a measurement object, receiving a voltage signal induced by the transmitted current signal from the measurement object, determining a target compensation signal that reduces a carrier frequency component in a voltage signal that is input into an amplifier based on an output signal of the amplifier into which the received voltage signal is input, applying the target compensation signal to the voltage signal, and amplifying the voltage signal to which the target compensation signal is applied, wherein the determining comprises determining a signal value of a subsequent compensation signal based on a signal value of the output signal of the amplifier that is amplified by applying a previous compensation signal to the output signal of the amplifier.

The determining of the target compensation signal may include searching for the target compensation signal based on a change in the output signal of the amplifier resulting from a change in a signal magnitude of the previous compensation signal.

The determining of the target compensation signal may include sampling a first signal value of a first output signal included in a differential output signal of the amplifier, and sampling a second signal value of a second output signal included in the differential output signal, comparing the sampled first signal value and the sampled second signal value, and determining a comparison result based on the comparing; and determining the signal value of the subsequent compensation signal based on the comparison result.

The determining of the target compensation signal may include sampling the signal value of the output signal of the amplifier, comparing the sampled signal value of the output signal of the amplifier to a reference signal value, and determining a comparison result based on the comparing, and determining the signal value of the subsequent compensation signal based on the comparison result.

The determining of the signal value of the subsequent compensation signal may include determining the signal value of the subsequent compensation signal to be greater than a signal value of the previous compensation signal, or to be less than the signal value of the previous compensation signal, based on the comparison result.

In a general aspect a method includes transmitting a current signal to a measurement object, receiving a voltage signal induced by the transmitted current signal from the measurement object, transmitting the voltage signal to an amplifier, generating a compensation signal based on an output from the amplifier, and determining a target compensation signal by gradually increasing the generated compensation signal by comparing two output values of a differential output of the amplifier.

Other features and aspects will be apparent from the following detailed description, the drawings, and the claims.

Figure 1:
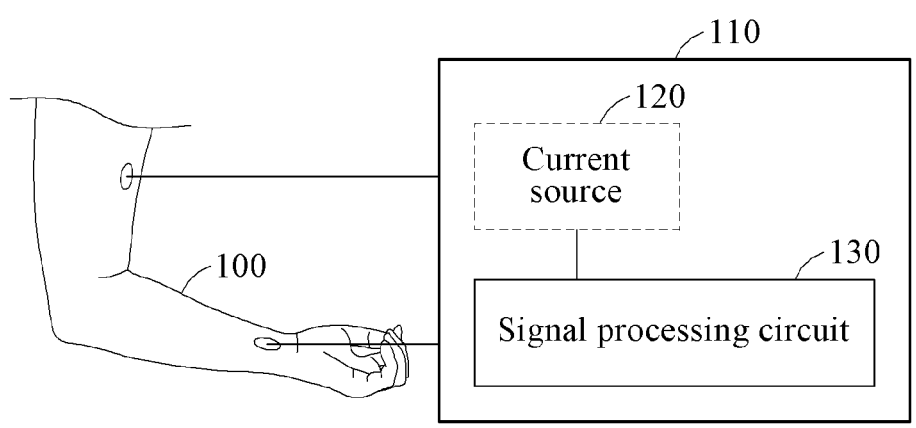
FIG. 1 illustrates an example of an overview of a signal measurement apparatus, in accordance with one or more embodiments.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

The features described herein may be embodied in different forms and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

The following structural or functional descriptions of examples disclosed in the present disclosure are merely intended for the purpose of describing the examples and the examples may be implemented in various forms. The examples are not meant to be limited, but it is intended that various modifications, equivalents, and alternatives are also covered within the scope of the claims.

Although terms such as first, second, and the like, are used herein to describe components, the components are not limited to the terms. Each of these terminologies is not used to define an essence, order, or sequence of a corresponding component but used merely to distinguish the corresponding component from other component(s). For example, a "first" component may be referred to as a "second" component, or similarly, and the "second" component may be referred to as the "first" component within the scope of the right according to the concept of the present disclosure. In addition, it should be noted that if it is described that one component is "connected", "coupled", or "joined" to another component, a third component may be "connected", "coupled", and "joined" between the first and second components, although the first component may be directly connected, coupled, or joined to the second component.

The singular forms "a", "an", and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

Unless otherwise defined, all terms used herein, including technical and scientific terms, have the same meanings as those generally understood. Terms, such as those defined in commonly used dictionaries, are to be interpreted as having a meaning that is consistent with their meaning in the context of the relevant art and the present disclosure, and are not to be interpreted in an idealized or overly formal sense unless expressly so defined herein.

Hereinafter, examples will be described in detail with reference to the accompanying drawings. Like reference numerals in the drawings denote like elements, and thus their description will be omitted.

FIG. 1 illustrates an example of an overview of a signal measurement apparatus, in accordance with one or more embodiments.

Referring to FIG. 1, a signal measurement apparatus 110 is an apparatus that measures a signal. The signal measurement apparatus 110, may for example, measure an impedance signal of a measurement object 100. The measurement object 100 is a living body. A signal measured from a living body is referred to as a biosignal, and the biosignal includes a bioelectric signal and a bioimpedance signal. The biosignal changes depending on a biological activity of the living body, for example, breathing, or a biological state of the living body. A state of the measurement object 100 is estimated based on a result of analyzing such a change in the biosignal. For example, the signal measurement apparatus 110 measures a biosignal obtained from the measurement object 100, and processes the measured biosignal so that the biosignal is in a form that is easy to analyze.

The signal measurement apparatus 110 includes a current source 120 configured to supply a current signal, for example, an alternating current signal, to the measurement object 100, and a signal processing circuit 130 configured to measure a voltage signal, for example, an alternating voltage signal, received from the measurement object 100 and process the measured voltage signal. In an example, the current source 120 may be provided separately from the signal measurement apparatus 110, rather than being included in the signal measurement apparatus 110. A magnitude, a frequency, and a signal waveform of the current signal supplied from the current source 120 may be previously known information. The current signal output from the current source 120 is transmitted to the measurement object 100 through an electrode pair attached to the measurement object 100 in a contact or non-contact manner. The signal measurement apparatus 110 senses the voltage signal induced by the current signal from the measurement object 100 through another electrode pair attached to the measurement object 100.

The signal processing circuit 130 is a circuit configured to process the sensed voltage signal. The signal processing circuit 130 includes an amplifier configured to amplify the voltage signal measured from the measurement object 100, a compensation signal generating circuit configured to generate a compensation signal, and a converter configured to sample a signal value of the voltage signal amplified by the amplifier and convert an analog signal to a digital signal based on the sampled signal value.

A predetermined current signal is applied to the measurement object 100 through the current source 120, and an impedance of the measurement object 100 is estimated by measuring a voltage signal induced by the current signal applied to the measurement object 100. For example, if a predetermined current signal I supplied to the measurement object 100 is known and a voltage signal V measured from the measurement object 100 is known, an impedance Z of the measurement object 100 is estimated according to Ohm's law (Z=V/I).

An impedance component included in the voltage signal measured from the measurement object 100 includes a static impedance component and a dynamic impedance component. The dynamic impedance component is an impedance component which corresponds to a change in a signal responding to breathing or stimulation and is an object of interest. Conversely, the static impedance component is an impedance component irrelevant to breathing or stimulation and is not an object of interest. If a static impedance component including a direct current impedance component is great, the proportion of the static impedance component in the measured voltage signal is also great. The range of an impedance component to be measured is in the form having an alternating current impedance component Rac with a minute change range based on a relatively great direct current impedance component Rdc, rather than the form with the range from "0" to a maximum impedance value Rmax. For example, an impedance R(t) measured over time t is in the form of a sum of a direct current impedance component Rdc and an alternating current impedance component Rac that changes over time t, as expressed by Equation 1 below.

$$R(t)=Rdc+Rac(t) \qquad \text{Equation 1:}$$

Before estimating the impedance Z of the measurement object 100, the signal measurement apparatus 110 amplifies the measured voltage signal through the amplifier included in the signal processing circuit 130. In a process of amplifying the measured signal, if the amplified signal is out of the range of the signal that may be processed by the signal processing circuit 130, saturation may occur where the amplified signal does not follow the change pattern of the originally measured signal and is fixed to a predetermined signal value. If saturation occurs, meaningful information included in the measured signal may not be used. Thus, saturation is not desirable. If the range of the signal that may be processed by the signal processing circuit 130 is designed to be wide to lower the probability of the occurrence of saturation, relatively high-performance elements may be necessary, which decreases the efficiency.

In an example, an operating voltage of a signal measurement circuit that performs signal measurement may decrease. In response to the decrease of the operating voltage, the signal range for measuring an analog signal is gradually limited. If the signal range that may be measured by the signal measurement circuit is narrow, a signal beyond the signal range may not be measured normally.

According to examples set forth hereinafter, the signal measurement apparatus 110 and a signal measurement method performed by the signal measurement apparatus 110 are provided. The signal measurement apparatus 110 minimizes the static component which is not an object of interest in the voltage signal measured from the measurement object 100 and performs signal processing principally on the dynamic component which is an object of interest. The signal measurement apparatus 110 reduces a magnitude of a direct current impedance component in the voltage signal to be amplified using a compensation signal and amplifies the voltage signal. Accordingly, the signal measurement apparatus 110 normally performs signal processing with respect to a voltage signal with a wider amplitude, without causing saturation of the circuit. The direct current impedance component not reflected in the amplification process may be restored later in a signal processing process for converting into a digital signal, or may not be used in some examples. Hereinafter, the signal measurement apparatus 110 and a signal measurement method performed by the signal measurement apparatus 110 will be described further.

Figure 2:
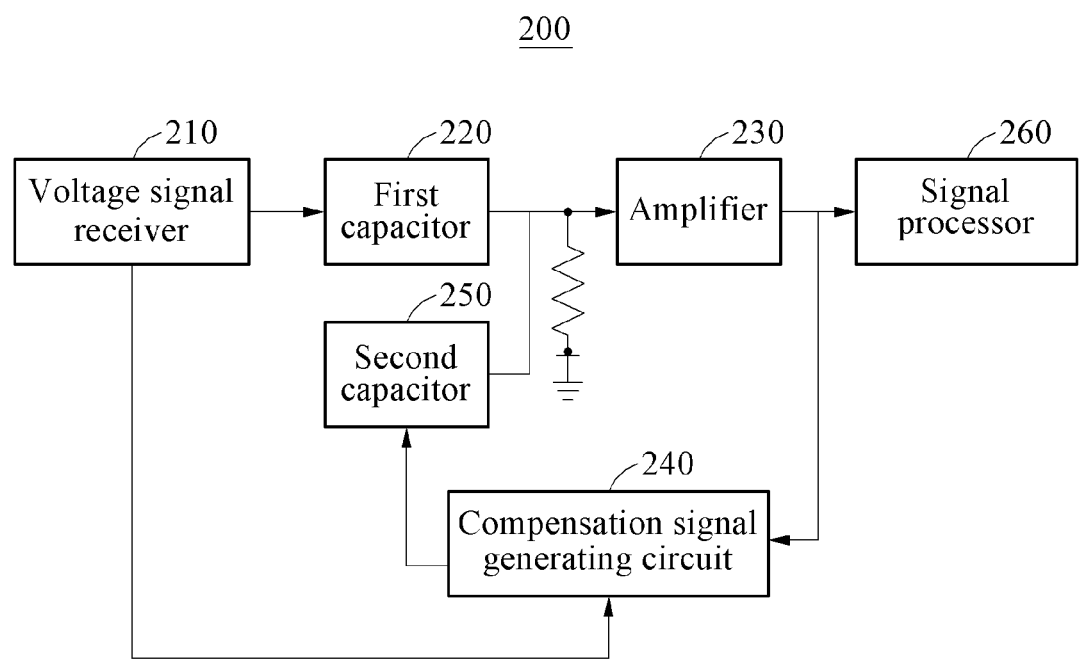
FIG. 2 illustrates an example of a configuration of a signal measurement apparatus, in accordance with one or more embodiments.

FIG. 2 illustrates an example of a configuration of a signal measurement apparatus, in accordance with one or more embodiments.

Referring to FIG. 2, a signal measurement apparatus 200 includes a voltage signal receiver 210, a first capacitor 220, an amplifier 230, a compensation signal generating circuit 240, a second capacitor 250, and a signal processor 260.

The voltage signal receiver 210 receives a voltage signal that is measured from a measurement object, for example measurement object 100 (FIG. 1). The received voltage signal may be in the form of a differential voltage signal. The voltage signal receiver 210 includes a current source (not shown) configured to supply a predefined current signal, for example, an alternating current signal with a predetermined carrier frequency, to the measurement object, and receive a differential voltage signal induced by the current signal from the measurement object. The differential voltage signal may include a first voltage signal of a first polarity, for example, a positive pole, and a second voltage signal of a second polarity, for example, a negative pole, different from the first polarity.

The voltage signal received by the voltage signal receiver 210 is transmitted to the compensation signal generating circuit 240 and to the first capacitor 220. The first capacitor 220 removes a direct voltage component from the received voltage signal, and outputs the resultant voltage signal. The voltage signal measured from the measurement object is transmitted to a first end of the first capacitor 220, and the second end of the first capacitor 220 is connected to an input terminal of the amplifier 230.

The amplifier 230 amplifies and outputs the voltage signal input through the input terminal of the amplifier 230. The amplifier 230 may be a differential amplifier. The differential amplifier is an amplifier configured to amplify a difference in an input differential voltage signal, and corresponds to, for example, an instrumentation amplifier (IA). The output signal of the amplifier 230 is transmitted to the compensation signal generating circuit 240 and the signal processor 260.

The compensation signal generating circuit 240 generates a compensation signal based on the received output signal of the amplifier 230. The compensation signal generating circuit 240 generates a target compensation signal to reduce a carrier frequency component in the voltage signal to be input into the amplifier 230 based on the output signal of the amplifier 230. The target compensation signal and the voltage signal transmitted from the first capacitor 220 are in antiphase. The generated target compensation signal is applied to the voltage signal transmitted from the first capacitor 220 via the second capacitor 250, and the voltage signal to which the target compensation signal is applied is input into the amplifier 230. In response to the target compensation signal being applied to the voltage signal transmitted from the first capacitor 220, a carrier signal component or a carrier frequency component in a signal to be input into the amplifier 230 is reduced. The amplifier 230 amplifies and outputs the voltage signal to which the target compensation signal is applied. A first end of the second capacitor 250 is connected to the compensation signal generating circuit 240 such that the compensation signal generated by the compensation signal generating circuit 240 is supplied to the capacitor 250, and a second end thereof is connected to the input terminal of the amplifier 230. The second end of the first capacitor 220, the second end of the second capacitor 250, and the input terminal of the amplifier 230 are connected to each other at a common node.

The compensation signal generating circuit 240 performs a process of searching for an optimal target compensation signal based on the output signal of the amplifier 230. The compensation signal generating circuit 240 determines an ultimate signal magnitude of the target compensation signal through the search process. To determine the optimal target compensation signal, the compensation signal generating circuit 240 adjusts a signal magnitude of a compensation signal based on the output signal of the amplifier 230, and searches for the optimal target compensation signal based on a change in the output signal of the amplifier resulting from a change in the signal magnitude of the compensation signal. The compensation signal may be a previous compensation signal that was generated after the receipt of the initial output signal of the amplifier 230. The compensation signal generating circuit 240 determines the signal magnitude of the compensation signal based on a comparison result obtained based on a signal value of the output signal of the amplifier 230, and generates and outputs a compensation signal of the determined signal magnitude. When determining the target compensation signal, the compensation signal generating circuit 240 performs a process of determining a signal value of a subsequent compensation signal based on the signal value of the output signal of the amplifier 230, which is amplified by applying a previous compensation signal. The process of searching for the optimal target compensation signal performed by the compensation signal generating circuit 240 will be described further with reference to FIGS. 3 through 8.

According to the example of applying the target compensation signal, Equation 1 is modified as expressed by Equation 2 below.

$$Rnew(t)=Rdc\_new+Rac(t)=[Rdc-Rc]+Rac(t) \quad \text{Equation 2:}$$

In Equation 2, Rc denotes an impedance component of a compensation signal to reduce a direct current impedance component in a voltage signal to be amplified. Rdc denotes the direct current impedance component of the voltage signal to be amplified, and Rac(t) denotes an alternating current impedance component of the measurement object with respect to time t. Rdc_new corresponds to Rdc−Rc, and denotes the direct current impedance component with reduced magnitude. Rnew(t) denotes an impedance signal with the direct current impedance component reduced by applying the target compensation signal.

As discussed above, the signal measurement apparatus 200 attenuates the carrier signal component at the input terminal of the amplifier 230, and amplifies and measures the alternating current impedance component which is an object of interest. The signal magnitude of the voltage signal to be input into the amplifier 230 is reduced as the carrier signal component is reduced, whereby the range of the signal that may be handled by the measurement circuit is expanded.

Referring again to FIG. 2, the signal processor 260 processes the output signal of the amplifier 230. For example, the signal processor 260 performs signal processing, such as sampling the signal value, for example, a peak value, in the output signal of the amplifier 230 and converts the sampled analog signal value to a digital signal. The sampling process is performed with respect to a result signal obtained by amplifying the voltage signal to which the target compensation signal is applied through the amplifier 230. In a time interval during which the optimal target compensation signal is searched for, the above signal processing process is not performed.

Figure 3:
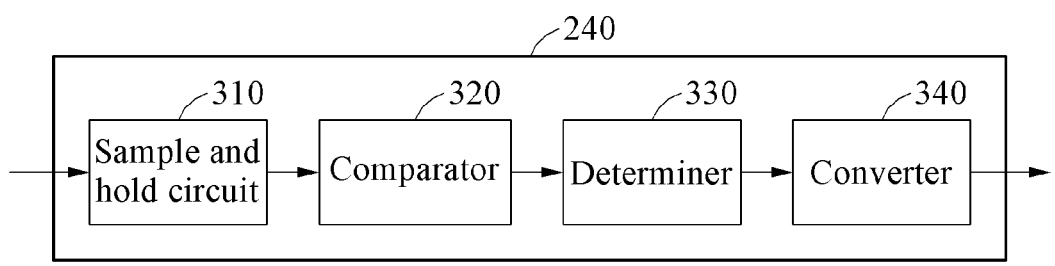
FIG. 3 illustrates an example of a configuration of a compensation signal generating circuit, in accordance with one or more embodiments.

FIG. 3 illustrates an example of a configuration of a compensation signal generating circuit in accordance with one or more embodiments.

Referring to FIG. 3, the compensation signal generating circuit 240 includes a sample and hold circuit 310, a comparator 320, a determiner 330, and a converter 340.

The sample and hold circuit 310 receives an output signal of an amplifier. The sample and hold circuit 310 samples a signal value of the output signal of the amplifier and holds the sampled signal value. The comparator 320 outputs a comparison result based on the signal value received from the sample and hold circuit 310. The determiner 330 determines a signal value of a compensation signal based on the comparison result output from the comparator 320. The converter 340 converts a signal value of a subsequent compensation signal, which is in the form of a digital signal, into an analog voltage signal, and outputs the analog voltage signal. The converter 340 includes a delayer (not shown) configured to delay a phase of the compensation signal. The analog voltage signal output from the converter 340 corresponds to the compensation signal generated by the compensation signal generating circuit 240.

In an example, the output signal of the amplifier 230 (FIG. 2) is an alternating current signal generated based on a carrier frequency component of a current output from a current source, wherein the sample and hold circuit 310 included in the compensation signal generating circuit 240 extracts envelope information of the alternating current signal. In another example, the sample and hold circuit 310 may be replaced with a circuit that may extract the envelope information of the alternating current signal from the output signal of the amplifier 230. For example, the sample and hold circuit 310 may be replaced with a peak detection circuit or an envelope detection circuit.

The compensation signal generating circuit 240 may perform the process of searching for the optimal target compensation signal using the above components. The compensation signal generating circuit 240 first generates and outputs an initial compensation signal based on a predefined initial parameter value. The initial compensation signal is supplied to an input terminal of the amplifier and applied to a voltage signal measured from a measurement object. The voltage signal to which the initial compensation signal is applied is amplified and output by the amplifier, and the output signal of the amplifier is transmitted to the sample and hold circuit 310. The sample and hold circuit 310 samples and holds a signal value of the output signal of the amplifier. The signal value sampled by the sample and hold circuit 310 is transmitted to the comparator 320. Assuming that the output signal of the amplifier is a differential output signal including a first output signal and a second output signal with different polarities, the comparator 320 compares a first signal value of the first output signal and a second signal value of the second output signal in the differential output signal. The comparator 320 outputs a first comparison result value, for example, a high logic value, in response to the first signal value being greater than the second signal value, and outputs a second comparison result value, for example, a low logic value, different from the first comparison result value in response to the first signal value being less than or equal to the second signal value. Provided that the amplifier operates in a single-ended mode to generate a single output signal, the comparator 320 compares the signal value of the output signal of the amplifier to a predefined reference signal value, for example, a threshold value. The comparator 320 outputs a first comparison result value, for example, a high logic value, in response to the signal value of the output signal of the amplifier being greater than the reference signal value, and outputs a second comparison result value, for example, a low logic value, in response to the signal value of the output signal being less than or equal to the reference signal value.

In response to the first comparison result value being received from the comparator 320, the determiner 330 determines the signal value of the subsequent compensation signal to be greater than a signal value of a previous compensation signal generated at a previous time. Conversely, in response to the second comparison result value being received from the comparator 320, the determiner 330 determines the signal value of the subsequent compensation signal to be less than the signal value of the previous compensation signal. In this example, a variation of the signal value applied to determine the signal value of the subsequent compensation signal is less than a variation of the signal value applied to determine the signal value of the previous compensation signal. For example, if the variation of the signal value applied to the previous compensation signal is "16", the variation of the signal value of the subsequent compensation signal is less than "16. As the process of determining the signal value of the compensation signal is repeated, the variation applied to determine the signal value of the subsequent compensation signal gradually decreases.

The converter 340 receives the signal value of the compensation signal from the determiner 330, and generates a compensation signal in the form of an analog signal based on the received signal value of the compensation signal. The generated compensation signal is supplied to the input terminal of the amplifier, and the voltage signal to which the compensation signal is applied is amplified by the amplifier. The output signal of the amplifier is transmitted again to the compensation signal generating circuit 240, and the compensation signal generating circuit 240 automatically finds a signal value of an optimal target compensation signal by repeating the above process. The process of searching for the signal value of the target compensation signal is performed, for example, a predefined number of times.

Figure 4:
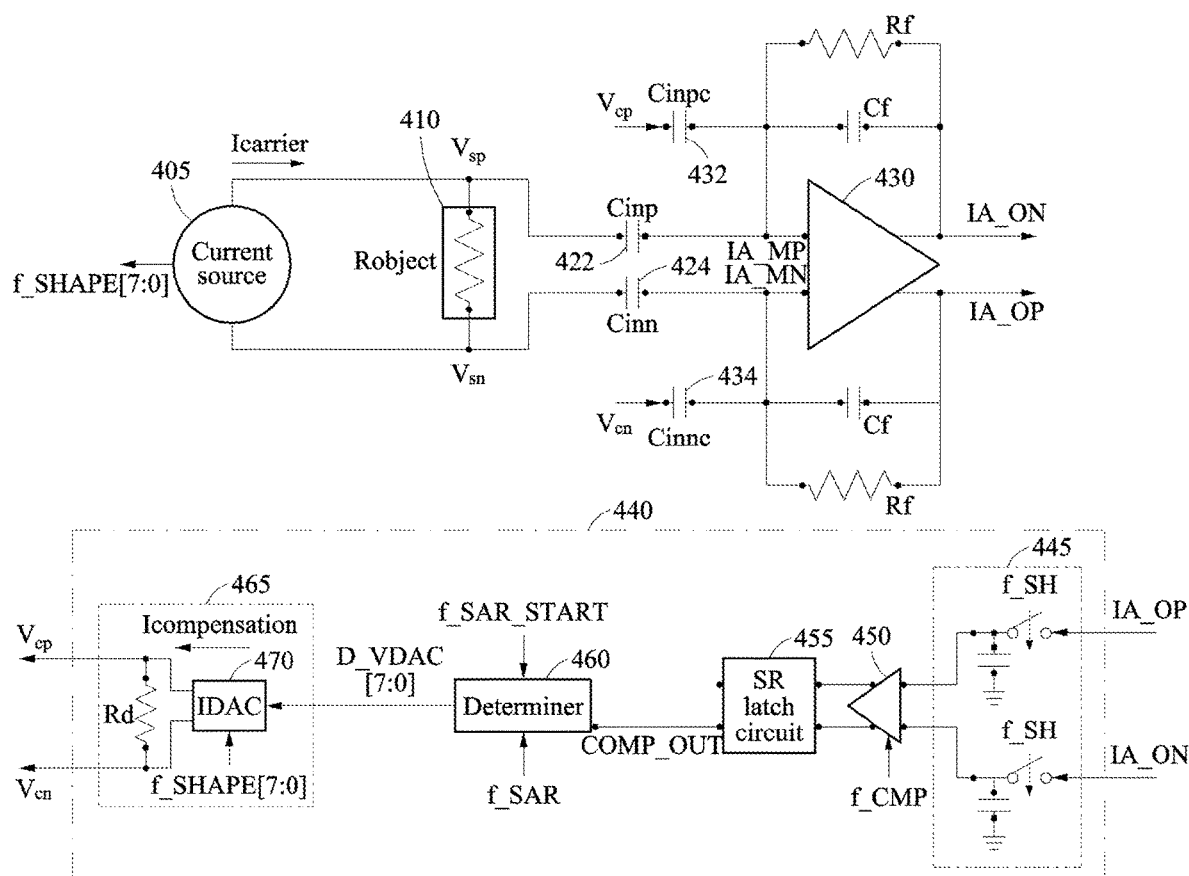
FIG. 4 illustrates an example of a circuit implementing a signal measurement apparatus, in accordance with one or more embodiments.

FIG. 4 illustrates an example of a circuit implementing a signal measurement apparatus in accordance with one or more embodiments.

Referring to FIG. 4, a current source 405 supplies a current signal Icarrier with a predetermined carrier frequency to a measurement object 410. Information related to the current signal Icarrier may be previously known. For example, information related to a waveform, a magnitude, and a frequency of the current signal Icarrier is predefined. In response to the current signal Icarrier being supplied to the measurement object 410, voltage signals $V_{sp}$ and $V_{sn}$ are induced by an impedance component Robject of the measurement object 410. A signal measurement apparatus senses the induced voltage signals $V_{sp}$ and $V_{sn}$ in the form of a differential voltage signal. In the circuit of FIG. 4, a terminal from which the current signal Icarrier is supplied to the measurement object 410, and a terminal at which the voltage signals $V_{sp}$ and $V_{sn}$ are received and measured, are illustrated to be bound as a common node. In reality, the terminal from which the current signal Icarrier is supplied, and the terminal at which the voltage signals $V_{sp}$ and $V_{sn}$ are received and measured, may be nodes which are arranged on the measurement object 410, and may be different from each other.

Further, if there are a plurality of current sources, a plurality of terminals at which current signals are supplied from the corresponding current sources may be positioned at different parts of the measurement object 410. Further, if there are a plurality of measurement channels for measuring voltage signals induced by the current signals, a plurality of terminals for measuring the voltage signals may be positioned at different parts of the measurement object 410.

The differential voltage signal sensed from the measurement object 410 is transmitted to capacitors Cinp 422 and Cinn 424. The capacitors Cinp 422 and Cinn 424 may remove direct voltage components from the sensed differential voltage signal, and output the resultant differential voltage signal to input terminals IA_MP and IA_MN of an amplifier 430. Signals of alternating voltage components included in the sensed differential voltage signal are transmitted to the input terminals IA_MP and IA_MN of the amplifier 430.

The amplifier 430 amplifies the signals transmitted to the input terminals IA_MP and IA_MN of the amplifier 430, and outputs the amplified signals. The output signals IA_ON and IA_OP of the amplifier 430 are transmitted to the compensation signal generating circuit 440 and a signal processor (for example, signal processor 260 in FIG. 2) for signal processing. In an example, the amplifier 430 may operate in a single-ended mode to receive a single voltage signal and generate a single output signal, or to receive a differential voltage signal and generate a single output signal. In an example of the amplifier 430 receiving a single voltage signal, the single voltage signal is input into one input terminal of the amplifier 430, and a reference voltage with a predetermined voltage value or a common mode signal of the single voltage signal is supplied to the other input terminal of the amplifier 430.

The compensation signal generating circuit 440 receives information related to the current signal Icarrier from the current source 405, and receives the output signals IA_ON and IA_OP from the amplifier 430. For example, the compensation signal generating circuit 440 receives a signal f_SHAPE including waveform information of the current signal Icarrier from the current source 405.

The compensation signal generating circuit 440 includes a sample and hold circuit 445, a comparator 450, an SR latch circuit 455, a determiner 460, and a converter 465. The sample and hold circuit 445 may include a switching device configured to sample signal values of the output signals IA_ON and IA_OP of the amplifier 430 based on a control signal f_SH activated with a predetermined cycle, and a capacitor device configured to hold the sampled signal values. For example, the sample and hold circuit 445 samples the signal values of the output signals IA_ON and IA_OP at each time corresponding to a 90-degree phase of the current signal Icarrier.

The sampled signal values are transmitted to the comparator 450. The comparator 450 compares the sampled signal values with respect to the output signals IA_ON and IA_OP received from the sample and hold circuit 445, based on a control signal f_CMP. The control signal f_CMP is a control signal to control a time at which the comparator 450 is to perform the comparison function. If the output signal of the amplifier 430 is in the form of a differential output signal, like the output signals IA_ON and IA_OP of the amplifier 430, the comparator 450 compares signal values of the sampled differential output signal at a predetermined time. For example, the comparator 320 compares a first signal value of the first output signal IA_ON and a second signal value of the second output signal IA_OP in the differential output signal, and outputs a first comparison result value, for example, a high logic value, or a second comparison result value, for example, a low logic value, based on a comparison result.

In an example, the SR latch circuit 455 stores or retains information related to the comparison result values output from the comparator 450. The SR latch circuit 455 transmits a comparison result value COMP_OUT determined by the comparator 450 to the determiner 460. The determiner 460 adjusts a signal value of a compensation signal based on the comparison result value COMP_OUT. The determiner 460 determines a signal value of a subsequent compensation signal to be generated. A control signal f_SAR_START input into the determiner 460 may be used to determine an operation start time of the determiner 460. For example, the determiner 460 operates at a rising edge time of the control signal f_SAR_START. The other control signal f_SAR input into the determiner 460 may be used to determine a cycle for the determiner 460 to update the determination with respect to the compensation signal based on the comparison result value COMP_OUT.

If the comparison result value COMP_OUT corresponds to a high logic value, the determiner 460 determines that the signal value of the compensation signal is still small and increases the signal value of the subsequent compensation signal to be greater than the signal value of the previous compensation signal. Conversely, if the comparison result value COMP_OUT corresponds to a low logic value, the determiner 460 determines that the signal value of the compensation signal is excessive and decreases the signal value of the subsequent compensation signal to be less than the signal value of the previous compensation signal. The determiner 460 transmits a signal D_VDAC corresponding to the determined signal value of the subsequent compensation signal to the converter 465. For example, the signal D_VDAC may be an 8-bit signal having a value ranging from "0" to "255". The signal D_VDAC is used to control the signal value or a signal magnitude of the compensation signal.

The converter 465 generates and outputs compensation signals $V_{cp}$ and $V_{cn}$ based on the signal D_VDAC received from the determiner 460. The converter 465 includes a current digital-to-analog converter (IDAC) 470, and the IDAC 470 generates and outputs a compensation current Icompensation based on the signal f_SHAPE and the signal D_VDAC. The signal f_SHAPE may be used to generate the compensation signals $V_{cp}$ and $V_{cn}$ as precise analog signals. The compensation current Icompensation flows through both ends of a resistor Rd, thereby reducing the compensation signal $V_{cp}$ and $V_{cn}$ of the voltage signal. The compensation signals $V_{cp}$ and $V_{cn}$ and the voltage signal transmitted through the capacitors Cinp 422 and Cinn 424 may be in antiphase.

The compensation signals $V_{cp}$ and $V_{cn}$ are respectively transmitted to the input terminals IA_MP and IA_MN of the amplifier 430 via capacitors Cinpc 432 and Cinnc 434. When the compensation signals $V_{cp}$ and $V_{cn}$ are applied to the differential voltage signal transmitted to the input terminals IA_MP and IA_MN of the amplifier 430 through the capacitors Cinp 422 and Cinn 424, a carrier signal component or a carrier frequency component in the signal input into the amplifier 430 may be reduced. The amplifier 430 amplifies and outputs the differential voltage signal to which the compensation signals $V_{cp}$ and $V_{cn}$ are applied, and the output signals IA_ON and IA_OP of the amplifier 430 are transmitted to the compensation signal generating circuit 440 again. The compensation signal generating circuit 440 repeats the above process until a target compensation signal having an optimal signal value is determined or a predetermined performance count is reached.

Figure 5:
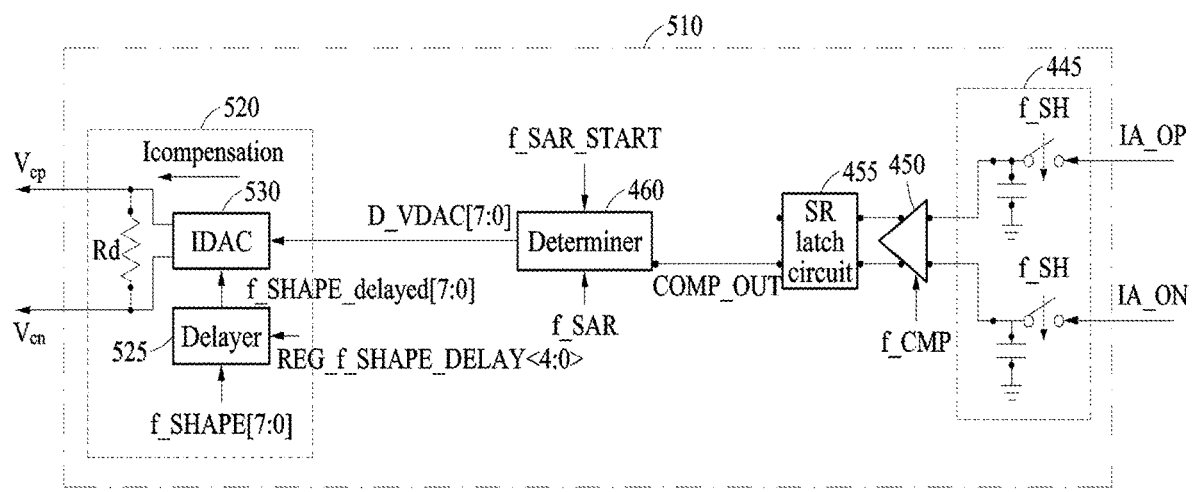
FIG. 5 illustrates an example of a circuit implementing a compensation signal generating circuit, in accordance with one or more embodiments.

FIG. 5 illustrates an example of a circuit implementing a compensation signal generating circuit in accordance with one or more embodiments.

Referring to FIG. 5, a compensation signal generating circuit 510 includes the sample and hold circuit 445, the comparator 450, the SR latch circuit 455, and the determiner 460 as illustrated in the example of FIG. 4. However, a converter 520 may include a IDAC 530 and may further include a delayer 525 configured to delay an output or a phase of a subsequent compensation signal. If there is another impedance component in addition to the impedance component Robject of the measurement object 410, there occurs a phase difference between the voltage signal to be input into the amplifier 430 and measured and the compensation signals $V_{cp}$ and $V_{cn}$, and the delayer 525 delays the phase of the compensation signal to reduce the phase difference. The delayer 525 generates a signal f_SHAPE_delayed by delaying a time or a phase of the signal f_SHAPE synchronized with the signal phase of the IDAC 530 based on a signal REG_f_SHAPE_DELAY including delay information. The delayed phase or time is a predefined fixed value.

Figure 6:
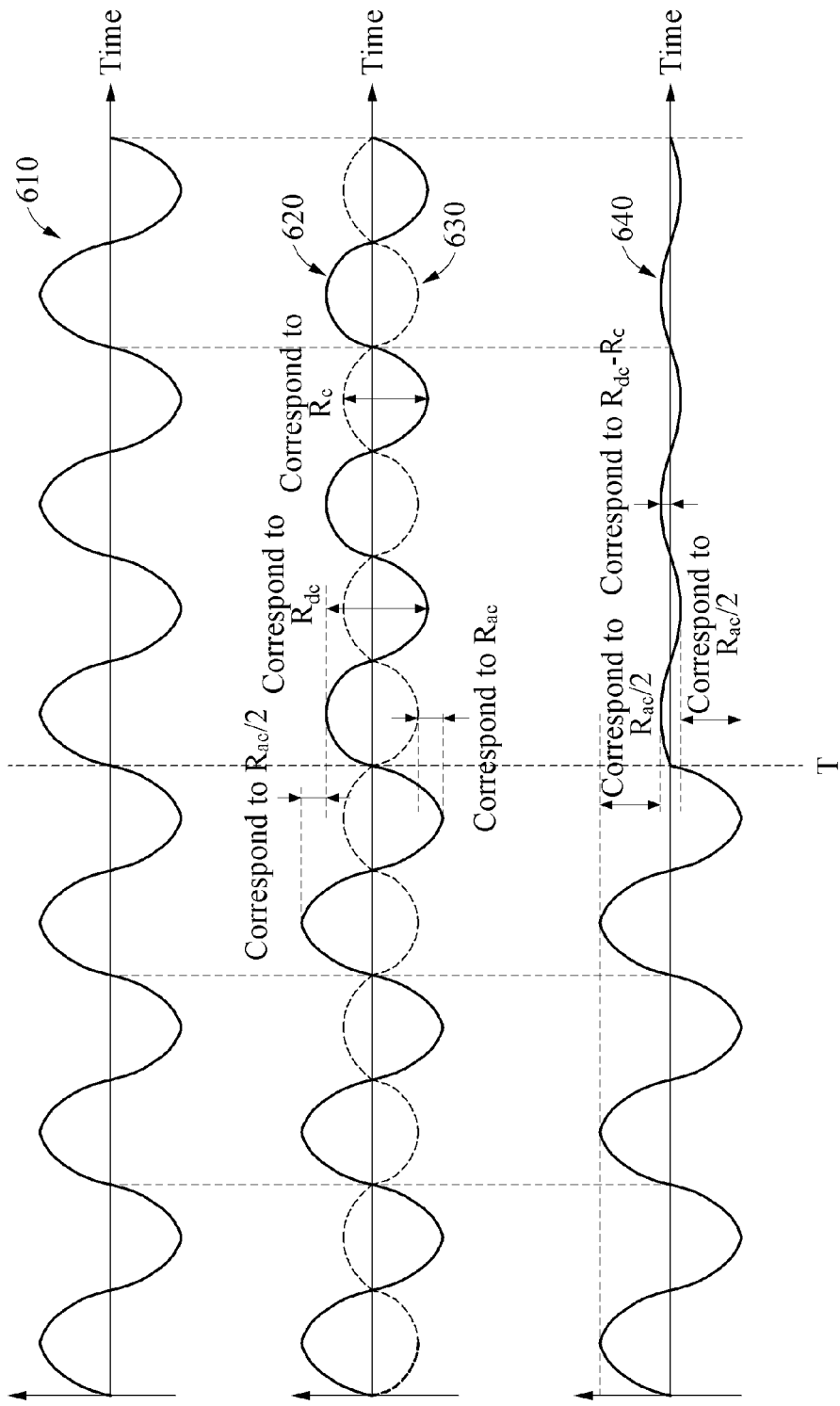
FIG. 6 illustrates an example of signal waveforms to describe an operation of a signal measurement apparatus, in accordance with one or more embodiments.

FIG. 6 illustrates an example of signal waveforms to describe an operation of a signal measurement apparatus in accordance with one or more embodiments.

The example of FIG. 6 will be described principally based on one side $V_{sp}$, $V_{cp}$ of a differential voltage signal for ease of description. The description will similarly apply to the other side $V_{sn}$, $V_{cn}$ of the differential signal.

Referring to FIG. 6, a signal waveform 610 may be a signal waveform of the current signal Icarrier output from the current source 405, and a signal waveform 620 indicated with a solid line may be a signal waveform of the voltage signal Vsp induced by supplying the current signal Icarrier to the measurement object 410. The signal waveform of the current signal Icarrier may be, for example, a sine wave. However, examples are not limited thereto. A signal waveform 630 may be a signal waveform of the compensation signal $V_{cp}$, and a signal waveform 640 may represent a voltage signal input into the amplifier 430 through the input terminal IA_MP of the amplifier 430. In the graphs showing the signal waveforms 610, 620, 630, and 640, the horizontal axis indicates a flow of time, and the vertical axis indicates a magnitude of a signal. The signal waveforms 610, 620, 630, and 640 are synchronized in terms of time, but have different scales of signal magnitude.

A measurement object has an impedance corresponding to Rdc+Rac before a time T, and the impedance of the measurement object is reduced by Rac after the time T, such that only an impedance corresponding to Rdc remains. In an example of a signal to which the compensation signal is not applied, that is, a signal not compensated as in the signal waveform 620, Rdc is overly great when compared to Rac, and thus a difference in magnitude of a carrier signal before and after the time T seems small. However, in an example of a signal to which the compensation signal is applied, that is, a signal compensated as in the signal waveform 630, a large portion of Rdc is attenuated by the compensation signal, and thus a change in the signal resulting from a change in Rac at the time T mat seem relatively large.

Figure 7:
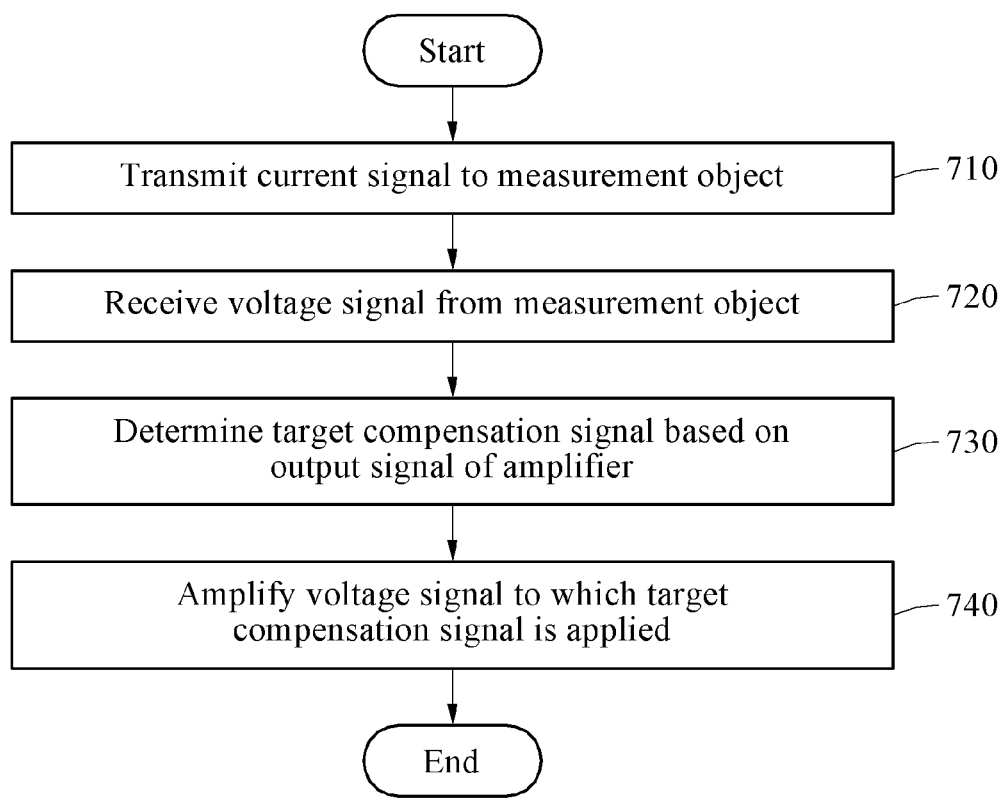
FIG. 7 illustrates an example of a signal measurement method, in accordance with one or more embodiments.

FIG. 7 illustrates an example of a signal measurement method. The operations in FIG. 7 may be performed in the sequence and manner as shown, although the order of some operations may be changed or some of the operations omitted without departing from the spirit and scope of the illustrative examples described. Many of the operations shown in FIG. 7 may be performed in parallel or concurrently. One or more blocks of FIG. 7, and combinations of the blocks, can be implemented by special purpose hardware-based computer that perform the specified functions, or combinations of special purpose hardware and computer instructions. In addition to the description of FIG. 7 below, the descriptions of FIGS. 1-6 are also applicable to FIG. 7, and are incorporated herein by reference. Thus, the above description may not be repeated here.

Referring to FIG. 7, in operation 710, a signal measurement apparatus transmits a current signal to a measurement object. The signal measurement apparatus transmits an alternating current signal with a predetermined carrier frequency to the measurement object through a current source.

In operation 720, the signal measurement apparatus receives a voltage signal induced by the transmitted current signal from the measurement object. For example, the signal measurement apparatus senses the signal measured from the measurement object in the form of a differential voltage signal. The differential voltage signal induced by the current signal includes an impedance characteristic of the measurement object.

In operation 730, the signal measurement apparatus determines a target compensation signal to reduce a carrier frequency component in a voltage signal to be input into an amplifier based on an output signal from the amplifier into which the voltage signal received in operation 720 is input. The signal measurement apparatus performs a process of searching for an optimal target compensation signal based on the output signal of the amplifier. The process of searching for the target compensation signal may include, for example, a process of determining a signal value of a subsequent compensation signal based on a signal value of the output signal of the amplifier which is amplified by applying a previous compensation signal. The signal measurement apparatus determines an ultimate signal magnitude of the target compensation signal through the search process. To determine the optimal target compensation signal, the signal measurement apparatus adjusts a signal magnitude of a compensation signal based on the output signal of the amplifier, and searches for the optimal target compensation signal based on a change in the output signal of the amplifier resulting from a change in the signal magnitude of the compensation signal.

In the process of determining the target compensation signal, the signal measurement apparatus samples a first signal value of a first output signal included in the differential output signal of the amplifier and samples a second signal value of a second output signal included in the differential output signal. The signal measurement apparatus compares the sampled first signal value and the sampled second signal value, determines a comparison result based on the comparing, and determines the signal value of the subsequent compensation signal based on the determined comparison result. In another example, in the process of determining the target compensation signal, the signal measurement apparatus samples the signal value of the output signal of the amplifier, and compares the sampled signal value to a predefined reference signal value. The signal measurement apparatus determines the signal value of the subsequent compensation signal based on the comparison result.

When determining the signal value of the subsequent compensation signal, the signal measurement apparatus determines the signal value of the subsequent compensation signal to be greater than a signal value of the previous compensation signal or to be less than the signal value of the previous compensation signal, based on the comparison result. The subsequent compensation signal determined as described above is supplied to the input terminal of the amplifier, and the process of amplifying the signal is performed by the amplifier again. The signal measurement apparatus determines whether the signal value of the compensation signal determined previously is appropriate based on the output signal of the amplifier, and continuously adjusts the signal value of the compensation signal until the target compensation signal with an optimal signal value is determined.

In operation 740, the signal measurement apparatus amplifies the voltage signal to which the target compensation signal determined in operation 730 is applied, by implementing the amplifier. The target compensation signal reduces a carrier frequency component in the voltage signal input into the amplifier. A signal processing process such as signal sampling and analog-to-digital conversion is performed with respect to the voltage signal amplified by the amplifier. The description provided with reference to FIGS. 1 through 6 applies to an operation of the signal measurement apparatus not described with reference to FIG. 7, and thus duplicated description will be omitted for conciseness.

Figure 8:
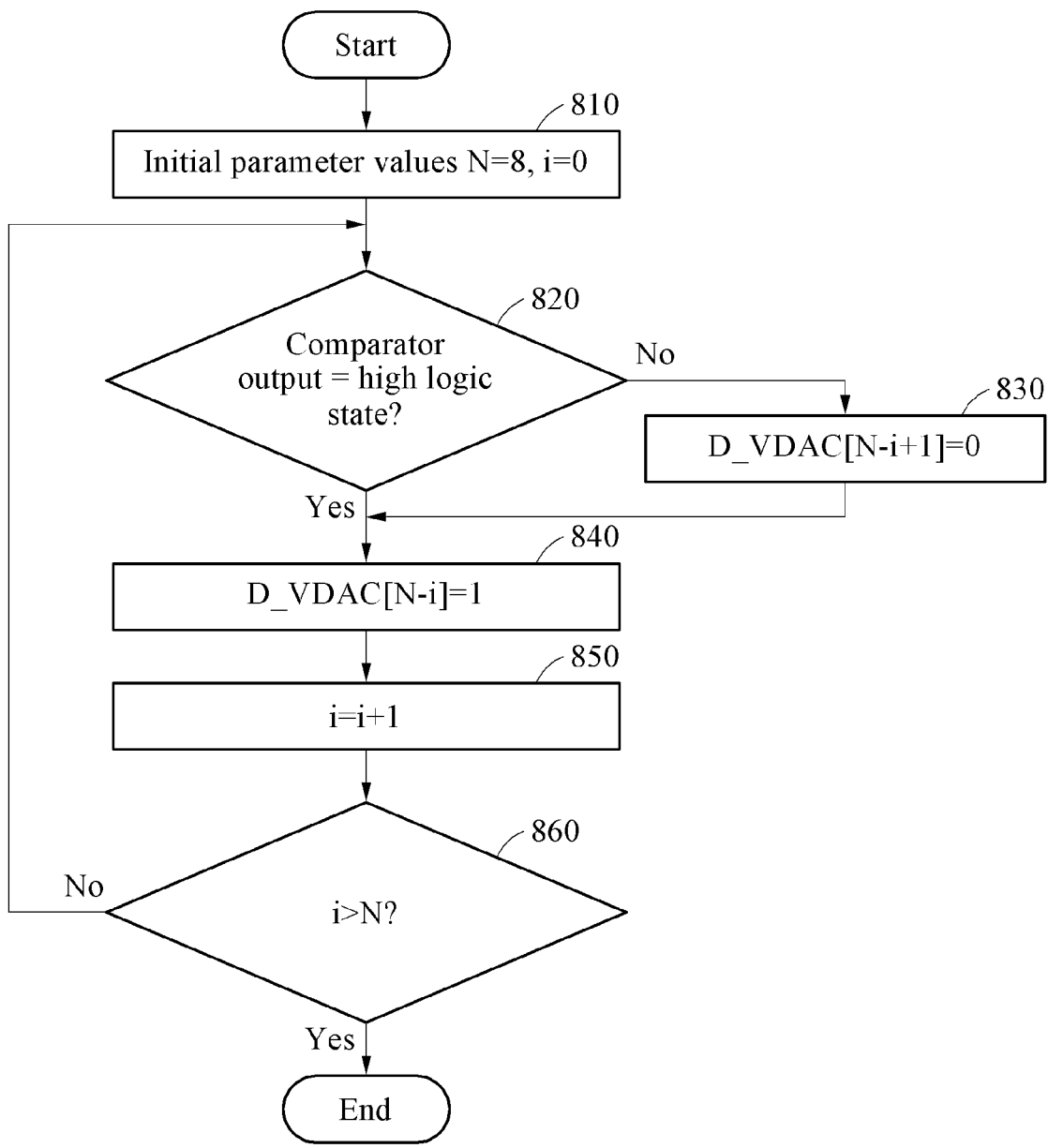
FIG. 8 illustrates an example of searching for a target compensation signal, in accordance with one or more embodiments.

FIG. 8 illustrates an example of searching for a target compensation signal. The operations in FIG. 8 may be performed in the sequence and manner as shown, although the order of some operations may be changed or some of the operations omitted without departing from the spirit and scope of the illustrative examples described. Many of the operations shown in FIG. 8 may be performed in parallel or concurrently. One or more blocks of FIG. 8, and combinations of the blocks, can be implemented by special purpose hardware-based computer that perform the specified functions, or combinations of special purpose hardware and computer instructions. In addition to the description of FIG. 8 below, the descriptions of FIGS. 1-7 are also applicable to FIG. 8, and are incorporated herein by reference. Thus, the above description may not be repeated here.

Referring to FIG. 8, the determiner 460 (FIG. 4) searches for an optimal signal value to be applied to a target compensation signal through a series of operations. In operation 810, initial parameter values are defined first. For example, initial parameter values N=8 and i=0 are defined.

In operation 820, the determiner 460 (FIG. 4) determines whether the comparison result value COMP_OUT with respect to the signal values output from the comparator 450 (FIG. 4), for example, signal values sampled with respect to the output signals IA_ON and IA_OP of the amplifier 430 (FIG. 4), is a first comparison result value, for example, a high logic state. In response to the comparison result value COMP_OUT determined by the comparator 450 (FIG. 4) being a second comparison result value, for example, a low logic state, the determiner 460 (FIG. 4) sets a signal D_VDAC defining the signal magnitude of the compensation signal, as expressed by D_VDAC[N−i+1]=0, in operation 830. In this example, a signal magnitude of a subsequent compensation signal is less than a signal magnitude of a previous compensation signal.

In response to the comparison result value COMP_OUT being the first comparison result value, for example, a high logic state, as a result of the determining in operation 820, the determiner 460 (FIG. 4) sets the signal D_VDAC as expressed by D_VDAC[N−i]=1, in operation 840. In this example, the signal magnitude of the subsequent compensation signal may be greater than the signal magnitude of the previous compensation signal.

In operation 850, the determiner 460 (FIG. 4) increases the value of the parameter i by "1".

In operation 860, the determiner 460 (FIG. 4) determines whether the value of the parameter i is greater than the value of the parameter N. In response to the value of the parameter i not being greater than the value of the parameter N, the determiner 460 (FIG. 4) returns to operation 820 and repeats the above process. In response to the value of the parameter i being greater than the value of the parameter N, the process of searching for an optimal signal magnitude for the target compensation signal is terminated.

In the example described above, the signal measurement apparatus may also measure an absolute value of impedance to be measured. For example, the compensation signal generating circuit 240 (FIG. 2), 440 (FIG. 4), and 510 (FIG. 5) outputs a signal D_VDAC[7:0] in the form of a digital signal to determine the magnitude of the compensation signal, and the output signal corresponds to an impedance component Rc of the compensation signal. Information related to [Rdc−Rc]+Rac which is an impedance component after being compensated by the compensation signal is obtained from the output signal of the amplifier 230 (FIG. 2), and the signal processor 260 (FIG. 2) restores information of Rdc+Rac which is an original impedance component from the information related to [Rdc−Rc]+Rac which is the impedance component after compensated and the information related to the impedance component Rc which is known from the signal D_VDAC[7:0].

The signal measurement apparatuses 110 and 200, the current source 120, signal processing circuit 130, voltage signal receiver 210, first capacitor 220, amplifier 230, second capacitor 250, compensation signal generating circuit 240, signal processor 260, sample and hold circuit 310, comparator 320, determiner 330, and converter 340 with respect to FIGS. 1-8, and that perform operations described in this application, are implemented as and by hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer.

Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods of FIGS. 1-8 that perform the operations described in this application are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. The instructions or software may be written using any programming language based on the block diagrams and the flow charts illustrated in the drawings and the corresponding descriptions in the specification, which disclose algorithms for performing the operations performed by the hardware components and the methods as described above.

The instructions or software to control computing hardware, for example, one or more processors or computers to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access programmable read only memory (PROM), electrically erasable programmable read-only memory (EEPROM), random-access memory (RAM), dynamic random access memory (DRAM), static random access memory (SRAM), flash memory, non-volatile memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, blue-ray or optical disk storage, hard disk drive (HDD), solid state drive (SSD), flash memory, a card type memory such as multimedia card micro or a card (for example, secure digital (SD) or extreme digital (XD)), magnetic tapes, floppy disks, magneto-optical data storage devices, optical data storage devices, hard disks, solid-state disks, and any other device that is configured to store the instructions or software and any associated data, data files, and data structures in a non-transitory manner and provide the instructions or software and any associated data, data files, and data structures to one or more processors or computers so that the one or more processors or computers can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A signal measurement apparatus comprising:
   a compensation signal generating circuit configured to:
      receive, as a first input, a voltage signal being measured from a measurement object directly from a voltage signal received, and received, as a second input, an output signal of an amplifier circuit; and
      generate, based on the output signal of the amplifier circuit, a target compensation signal that is combined with the voltage signal to compensate the voltage signal for reducing a carrier frequency component in the voltage signal that is input into the amplifier circuit, the generating including adjusting a signal value of the target compensation signal dependent on a change in a signal magnitude of a previous compensation signal;

the amplifier circuit configured to amplify the voltage signal with which the target compensation signal is combined; and the compensation signal generating circuit configured to determine a signal value of a subsequent compensation signal based on a signal value of the output signal of the amplifier circuit that is amplified by applying the previous compensation signal to the output signal of the amplifier circuit, when determining the target compensation signal.

2. The signal measurement apparatus of claim 1, wherein the compensation signal generating circuit is further configured to determine the target compensation signal based on a change in the output signal of the amplifier circuit resulting from the change in the signal magnitude of the previous compensation signal.

3. The signal measurement apparatus of claim 1, wherein the compensation signal generating circuit comprises:
 a sample and hold circuit configured to sample the signal value of the output signal of the amplifier circuit and hold the sampled signal value;
 a comparator configured to receive the signal value from the sample and hold circuit and output a comparison result; and
 a determiner configured to determine the signal value of the subsequent compensation signal based on the comparison result.

4. The signal measurement apparatus of claim 3, wherein the comparator is further configured to:
 compare a first signal value of a first output signal of the amplifier circuit and a second signal value of a second output signal of the amplifier circuit, the first output signal and the second output signal included in a differential output signal of the amplifier circuit,
 output a first comparison result value in response to the first signal value being greater than the second signal value, and
 output a second comparison result value different from the first comparison result value in response to the first signal value being less than or equal to the second signal value.

5. The signal measurement apparatus of claim 4, wherein the determiner is further configured to determine the signal value of the subsequent compensation signal to be greater than a signal value of the previous compensation signal, in response to the first comparison result value being received from the comparator.

6. The signal measurement apparatus of claim 4, wherein the determiner is further configured to determine the signal value of the subsequent compensation signal to be less than a signal value of the previous compensation signal, in response to the second comparison result value being received from the comparator.

7. The signal measurement apparatus of claim 6, wherein a variation of a signal value applied to determine the signal value of the subsequent compensation signal is less than a variation of a signal value applied to determine the signal value of the previous compensation signal.

8. The signal measurement apparatus of claim 3, wherein the comparator is further configured to:
 compare the signal value of the output signal of the amplifier circuit to a reference signal value,
 output a first comparison result value in response to the signal value of the output signal of the amplifier circuit being greater than the reference signal value, and
 output a second comparison result value different from the first comparison result value in response to the signal value of the output signal of the amplifier circuit being less than or equal to the reference signal value.

9. The signal measurement apparatus of claim 3,
 wherein the subsequent compensation signal is a digital signal, and
 wherein the compensation signal generating circuit further comprises:
 a converter configured to convert the determined signal value of the subsequent compensation signal into an analog voltage signal.

10. The signal measurement apparatus of claim 9, wherein the converter comprises:
 a delayer configured to delay a phase of the subsequent compensation signal.

11. The signal measurement apparatus of claim 1, further comprising:
 a first capacitor comprising a first end to which the voltage signal measured from the measurement object is transmitted, and a second end connected to an input terminal of the amplifier circuit.

12. The signal measurement apparatus of claim 11, wherein the target compensation signal and the voltage signal transmitted from the first capacitor are in antiphase.

13. The signal measurement apparatus of claim 1, further comprising:
 a second capacitor comprising a first end connected to the compensation signal generating circuit, and a second end connected to an input terminal of the amplifier circuit.

* * * * *